United States Patent [19]

Stepaniuk et al.

[11] Patent Number: 4,918,168

[45] Date of Patent: Apr. 17, 1990

[54] PROCESS FOR THE CONTINUOUS DIAZOTIZATION OF AMINES IN A MULTI-STAGE REACTOR

[75] Inventors: Nickolas J. Stepaniuk, Chesterfield; Bruce J. Lamb, St. Charles, both of Mo.

[73] Assignee: Mallinckrodt Inc., St. Louis, Mo.

[21] Appl. No.: 124,500

[22] Filed: Nov. 24, 1987

[51] Int. Cl.$^4$ .................. C07C 113/04; C07C 113/00
[52] U.S. Cl. ..................................... 534/565; 534/579
[58] Field of Search ............................... 534/565, 579

[56] References Cited

U.S. PATENT DOCUMENTS

| | | | |
|---|---|---|---|
| 3,117,954 | 1/1964 | Hupfer | 534/565 |
| 3,423,391 | 1/1969 | Kindler et al. | 534/565 |
| 4,018,751 | 4/1977 | Trecek | 534/565 X |
| 4,233,213 | 11/1980 | Breig et al. | 534/565 |
| 4,234,478 | 11/1980 | Atherton et al. | 534/565 X |
| 4,246,171 | 1/1981 | Hamilton et al. | 534/565 |
| 4,268,437 | 5/1981 | Behringer et al. | 534/565 |
| 4,737,349 | 4/1988 | Arnold et al. | 534/565 X |

FOREIGN PATENT DOCUMENTS

| | | | |
|---|---|---|---|
| 0209492 | 1/1987 | European Pat. Off. | 534/565 |
| 2825655 | 12/1979 | Fed. Rep. of Germany | 534/565 |

OTHER PUBLICATIONS

C & E News, vol. 39, pp. 65 and 67 (1961).

Primary Examiner—Floyd D. Higel
Attorney, Agent, or Firm—Bernard, Rothwell & Brown

[57] ABSTRACT

Disclosed is a process for continuous preparation of aromatic diazonium fluoride salts wherein diazotizable aromatic primary amines are continuously diazotized in a reactor containing a plurality of sequential reaction zones, wherein a portion of the diazotization agent is continuously injected into each of the reaction zones.

22 Claims, 3 Drawing Sheets

PROCESS FOR THE CONTINUOUS DIAZOTIZATION OF AMINES IN A MULTI-STAGE REACTOR

BACKGROUND OF THE INVENTION

This invention relates to a process for continuous preparation of aromatic diazonium fluoride salts wherein diazotizable aromatic primary amines are continuously diazotized in a reactor containing a plurality of sequential reaction zones, such as a tubular cross-flow reactor.

Diazotization of aromatic primary amines to prepare aromatic diazonium fluorides is of considerable importance in that such diazonium compounds are intermediates which can be converted to dyes (e.g. amino azobenzene) and aromatic fluorides which are useful as intermediates in preparing various pesticides, pharmaceuticals and other products.

Processes have heretofore been proposed for continuous diazotization of aromatic primary amines. Hupfer, U.S. Pat. No. 3,117,954 discloses a process for continuous diazotization of amines wherein the diazotization is carried out in several cascaded stirring vessels or several vessels arranged in series or in combination of the two kinds of plants. The end point of the diazotization reaction is potentiometrically monitored and additional amine and nitrous acid reactants are added in response to maintain a constant measured potential.

Kindler, U.S. Pat. No. 3,423,391 discloses a process for the continuous diazotization, particularly at relatively high temperatures, of amines with diazotization agents and for the further reaction of the resultant diazo compounds or allegedly for their recovery as such. However, the patent discloses that the diazo compounds obtained are separated or further reacted so rapidly that no appreciable amounts of decomposition products can form. According to the patent, substantially all (e.g. at least 50%) of the heat of reaction from the continual mixing and reacting of the amine and the diazotization agent is absorbed by the reaction mixture, the temperature thereof rising by from 20° C. to 50° C. or more, and the diazo compounds formed are obtained at 40° C. to 80° C. or, in case of high melting point or sparingly soluble components, to 100° C. or even higher. In a favored embodiment (illustrated in FIG. 1 and described in Columns 3–4 thereof) for a substantially adiabatic reaction, diazotization agent, amine or amine salt to be diazotized, and acid (if required) flow from separate reservoirs into a flow tube. According to the patent: "The materials are mixed here, for example, by means of a nozzle 11, and reacted during a short residence period and without cooling, i.e. with a rise in temperature." The diazo compounds may then be further processed in an immediately adjacent circulation system 12. Such embodiment is illustrated in Example 4 of the patent, which discloses flows from three separate reservoirs of (1) a solution of hydrogen chloride in water, (2) p-chloroaniline, and (3) a solution of sodium nitrate in water, which are mixed in the flow tube. According to such Example 4, the temperature of the three reactants upon entry into the reactor is 89° C., and after a reaction period of about 0.2 second, the boiling diazo solution leaves the reactor at about 100° C. In another embodiment (shown in FIG. 2 of Kindler), combination of the reacting components takes place in a very short tube by means of a nozzle which sprays the reaction mixture tangentially onto the inner wall of a cyclone type container 12 in which it flows down in a spiral path and further reacts during a short residence period. Such embodiment is illustrated for aniline in the patent's Example 6, wherein the temperature of the resulting diazo solution was 55° C. in the lower part of the container.

U.S. Pat. No. 4,246,171 (Hamilton, et al) discloses a continuous diazotization process in which the rate of addition of the inorganic nitrite is controlled by a polarovoltric method. An aqueous solution of an amine in an acid and a solution of an inorganic nitrite are added continuously and regularly to a reactor. The addition of the solution of inorganic nitrite is automatically regulated to ensure that a preselected concentration of unreacted nitrous acid is maintained in the reactor throughout the entire reaction period.

Behringer, et al (U.S. Pat. No. 4,268,437) discloses a process for the continuous diazotization of primary aromatic amines by reacting an aqueous solution or suspension of the amine in a mineral acid with an aqueous sodium nitrite solution. The process comprises: supplying continuously the lower portion of cylindrical diazotization vessel placed in upright position with an aqueous mineral acid solution or suspension of a diazotizable primary aromatic amine and supplying the vessel simultaneously, via one or more inlets arranged one above the other so as to open laterally thereto, with an aqueous sodium nitrite solution, the amine and nitrite being used in stoichiometric proportions, or the nitrite being used in a stoichiometric deficiency and the acid being used in an excess of about 1 to 3 equivalents per amine equivalent in the mineral acid solution; reacting the resulting mixture with agitation and producing a laminar flow of liquid matter at temperatures of about 5° C. to 30° C.; removing reaction mixture from the upper portion of the diazotization zone at a place where the reaction mixture is substantially free from nitrous acid; filtering the reaction mixture removed and delivering diazonium salt-containing solution to a sojourn zone.

As described therein, if the amine undergoes diazotization slowly, it is good practice to introduce the aqueous sodium nitrite through a plurality of inlets disposed at different levels. According to Example 2 (using 3-nitro-4-amino toluene as the amine), sodium nitrite solution was continuously supplied through three inlets in quantities increasing from above to below. This is in contrast to the disclosure in Column 2, Lines 45-49 of Behringer, et al, recommending use of quantities decreasing from above to below so as to have a minor excess proportion of nitrous acid just in the reaction mixture formed within the region of the uppermost inlet.

Trecek, U.S. Pat. No. 4,018,751 describes a continuous process for producing aminoazobenzenes in a tubular reactor. A reaction stream comprising a large excess of an aromatic primary amine, a mineral acid and water is mixed with a second reaction stream comprising an aqueous solution of an alkali metal nitrite. The combined premixed streams are then continuously passed through a tubular reactor. The exit stream from the reactor comprises aminoazobenzene compound, which is recovered therefrom. According to the patent, in the tubular reactor, a portion of the amine diazotizes to form the corresponding diazonium salt which instantaneously couples with the unreacted (excess) amine to form the diazoamino compound, which rearranges under the acidic reaction conditions to form the aminoazo compound. The residence time in the reactor is less than about 10 minutes and the reaction temperature is between 40° C.-100° C. Reaction time is typically about 1-10 minutes.

However, the heretofore known continuous diazotization processes have not been entirely satisfactory in that they typically are complex, inefficient, expensive, and/or prone to result in an unacceptably high level of tar and/or other byproducts especially upon reaction of the diazotized amine products thereof to various other products. Accordingly, there is a substantial need in the art for a continuous diazotization process which would overcome the disadvantages of heretofore known processes.

The present invention substantially fulfills the above need and overcomes the above-noted deficiencies of the prior art in a simple, efficient and inexpensive manner by providing a continuous process wherein an aromatic amine is continuously diazotized to a diazonium fluoride in the presence of hydrogen fluoride in a multi-stage tubular reactor with close control of temperature throughout the reaction mixture.

DESCRIPTION OF THE INVENTION

Generally stated, the present invention provides a process for continuous preparation of an aromatic diazonium fluoride selected from carbocyclic and heterocyclic aromatic mono-(diazonium fluoride) and bis-(diazonium fluoride) compounds from the corresponding aromatic amine selected from diazotizable carbocyclic and heterocyclic aromatic primary monoamine and diamine compounds. In accordance with the process of the invention, the aromatic amine is continuously introduced into a multi-stage reactor comprising a plurality of sequential reaction zones; a diazotization agent such as nitrosyl fluoride is continuously introduced into each reaction zone and admixed therein with aromatic amine, thereby reacting a portion of the aromatic amine with nitrosyl fluoride to form aromatic diazonium fluoride; and controlling the temperature in each reaction zone such that the maximum temperature of the reaction mixture in each reaction zone is less than the autothermal decomposition temperature of the mixture and that the diazonium fluoride undergoes substantially no thermal decomposition. The ratio of the flow rate of aromatic amine into the multi-stage reactor to the sum of the flow rates of nitrosyl fluoride into the plurality of reaction zones is such that at least 95 mole % of the nitrosyl fluoride is reacted to form diazonium fluoride.

By introducing the diazotization agent (nitrosyl fluoride) in portions in successive reaction stages and controlling the temperature in each stage to maintain the desired reaction temperature, it is possible to employ relatively thinner-walled materials of construction for the reactor than are required by prior art processes without danger of a runaway reaction. Furthermore, the process of the invention can be carried out with little or no production of undesirable by-products.

A preferred embodiment of the invention comprises:
(a) continuously introducing a flow of a solution of aromatic amine in hydrogen fluoride into a cross-flow tubular reactor, said cross-flow tubular reactor comprising a plurality of sequential reaction zones;
(b) continuously introducing into the upstream portion of each reaction zone a flow of nitrosyl fluoride;
(c) mixing the amine solution and the nitrosyl fluoride in each reaction zone, thereby reacting the amine and the nitrosyl fluoride to form aromatic diazonium fluoride; and
(d) removing heat from one or more of the reaction zones at a sufficient rate that the maximum temperature of the mixture in each reaction zone is less than the autothermal decomposition temperature of a said mixture and that the diazonium fluoride undergoes substantially no thermal decomposition, provided that the ratio of the flow rate of aromatic amine into the cross-flow tubular reactor to the sum of the flow rates of nitrosyl fluoride into the sequential reaction zones is such that at least 95 mole % of the nitrosyl fluoride is reacted to form diazonium fluoride.

DETAILED DESCRIPTION OF THE PREFERRED EMBODIMENT

Figure 1:
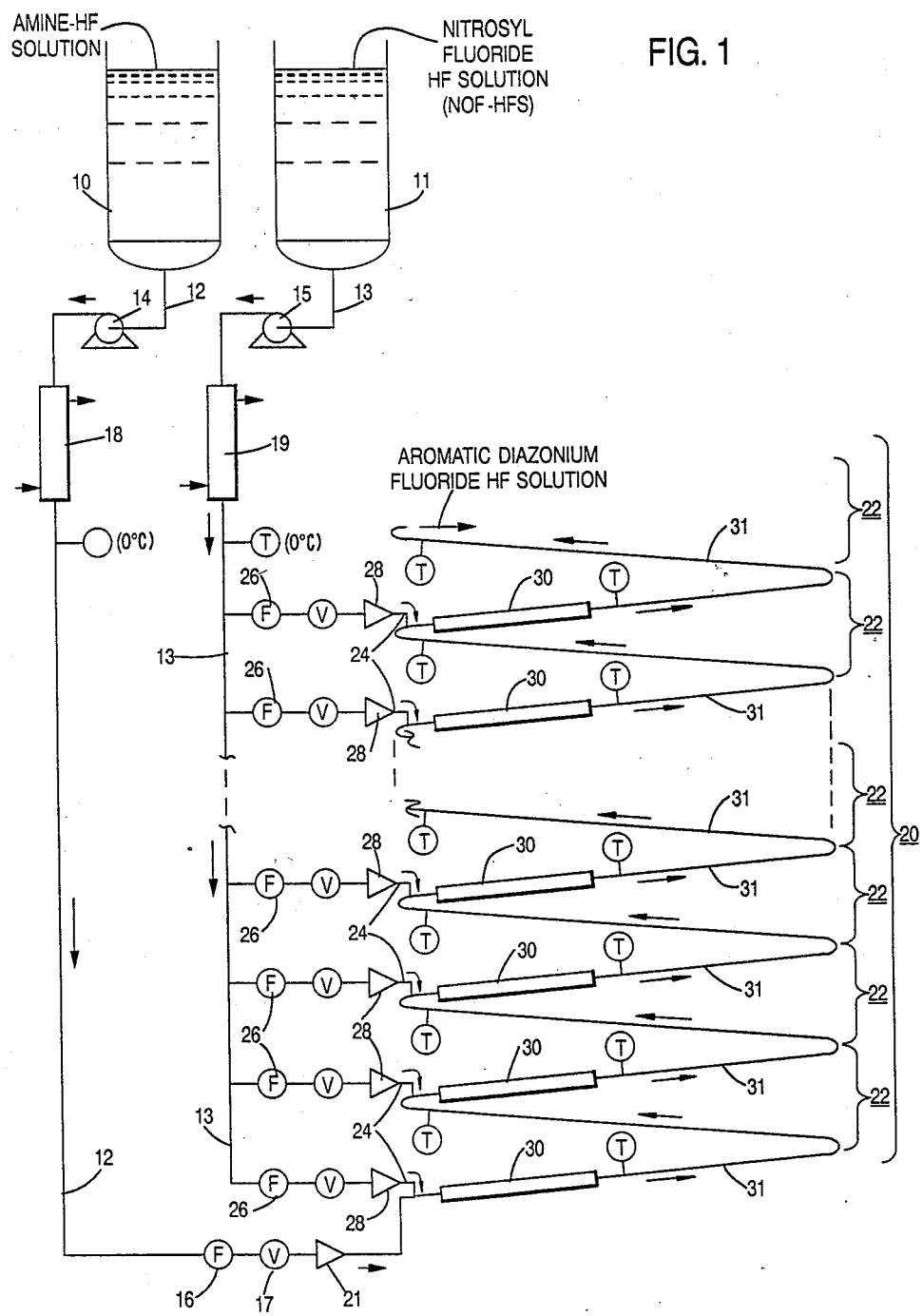
FIG. 1 is a schematic flow diagram of the process wherein a static mixer is employed in each reaction zone or section of a cross-flow tubular reactor.
Figure 2:
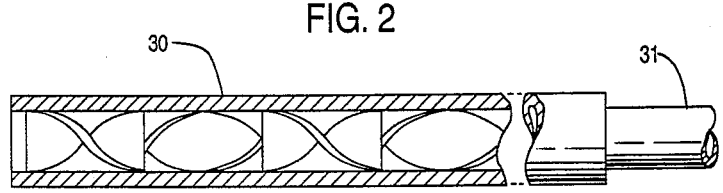
FIG. 2 is a fragmentary view, partly in section, showing a portion of a reaction section including its static mixer in greater detail.

The process of the present invention may be used for all aromatic amines which are diazotizable by reaction with nitrosyl fluoride under HF acid conditions. Such diazotizable aromatic amines include diazotizable carbocyclic aromatic primary amines (e.g. aminobenzenes) and heterocyclic aromatic primary amines (e.g. amino pyridines), including heterocyclic aromatic primary amines containing structures wherein benzene is condensed with a heterocyclic ring. Included by such amines are carbocyclic and heterocyclic mono-amines and carbocyclic and heterocyclic polyamnnes (e.g. diamines). Such amines include, for example, amines derived from such carbocyclic aromatic compounds as benzene, biphenyl, diphenylmethane, diphenyl ether, condensed benzenoids such as naphthalene and anthracene, and from such heterocyclic aromatic compounds as pyridine, quinoline and isoquinoline. The aromatic ring or rings in the aromatic amines may be unsubstituted or substituted with one or more substituents selected from the group consisting of alkyl (e.g. linear or branched alkyl having 1 to 12, preferably 1 to 4, carbon atoms), alkoxy (e.g. linear or branched alkoxy having 1 to 12, preferably 1-4, carbon atoms), halo (e.g. chloro, fluoro and bromo), nitro, cyano, acyl (e.g. linear or branched acyl having 1-4 carbon atoms, such as acetyl), acylamino (e.g. acetylamino), carboxy and hydroxy.

Suitable carbocyclic aromatic primary amines include, for example, aniline; methoxyaniline (e.g. para-anisidine); chloroaniline and bromoaniline in which the chloro or bromo group is in the ortho, meta or para position relative to the amine group; toluidines such as ortho-, meta- and para-aminotoluene, and ring-halogenated (e.g. ring-chlorinated or ring-brominated) derivatives of such toluidines, e.g.2-chloro-6-aminotoluene (also called 6-chloro-ortho-toluidine); ortho-, meta- and para-phenylene diamine; methylene dianilines such as 3,3'- 4,4'- and 3,4'-methylene dianiline; biphenyl amines, e.g. 2-amino-biphenyl, 4-amino-biphenyl, 3,3'-diamino-biphenyl, 4,4'-diamino-biphenyl and 3,4'-diamino biphenyl; and ring-halogenated biphenyl amines, e.g. 3,3'-dichloro-4,4'-diamino-biphenyl (i.e. 3,3'-dichlorobenzidine, which rapidly undergoes diazotization). Suitable heterocyclic aromatic primary amines include, for example, 2-, 3- and 4-aminopyridine; diaminopyridines such as 2,6-diaminopyridine; haloaminopyridine such as 2-amino-4,5- and 6-chloropyridine and 3-amino-5- and 6-chloropyridine; nitroaminopyridines such as 2-amino-5-nitropyridine; and alkylaminopyridines such as 2-amino-4,5- and 6-methylpyridine and 2-amino-4,6-dimethylpyridine.

In a preferred embodiment of this invention, the aromatic amine is aniline and the resulting diazotized amine is benzene diazonium fluoride, which can be decomposed to fluorobenzene (also called phenyl fluoride), which is useful as an intermediate for preparing insecticides, larvacides and tranquilizers. In another preferred embodiment, the aromatic amine is 6-chloro-ortho-toluidine and the resulting diazotized amine is 6-chloro-ortho-toluene diazonium fluoride, which can be decomposed to 2-chloro-6-fluorotoluene, which is useful as an intermediate for preparing herbicides and pharmaceuticals. In still another preferred embodiment, the aromatic amine is 4-fluoroaniline and the resulting 4-fluorobenzene diazonium fluoride can be decomposed to 1,4-difluorobenzene, which is useful as an intermediate for preparing herbicides.

Preferably, the amine is dissolved in a sufficient amount of HF such that all the amine will remain dissolved at 0° C. Such amount of HF is as follows for the indicated amines:

| Amine | Moles HF/Mole of Amine |
|---|---|
| Aniline | 6:1 |
| 2-chloro-o-toluidine | 6:1 |
| 4-fluoroaniline | 6:1 |
| Methylene dianiline | 9:1 |

The corresponding amounts for other amines can be readily determined by those skilled in the art.

A liquid amine-HF solution is formed using techniques in keeping with known methods for handling HF. Preferably, the solution is formed in a vessel having internal surfaces which are resistant to degradation by HF. Such surfaces may be formed, for example, of stainless steel and preferably polytetrafluoroethylene. The aromatic amine is added with stirring to sufficient liquid HF to prepare an amine-HF solution wherein the resulting dissolved amine will remain dissolved at 0° C.

The nitrosyl fluoride which is introduced into the reaction zones in accordance with the process of the invention can be provided in the form of a solution in a suitable solvent. Preferably, the nitrosyl fluoride is provided as a solution in HF. To form the solution, a diazotization agent which contains or forms NO+ (the nitrosonium ion) is added with stirring to sufficient liquid HF to prepare a solution of nitrosyl fluoride in HF having a concentration such that all of the dissolved agent will remain dissolved at 0° C. Suitable diazotization agents include, for example, alkali metal nitrite (e.g. sodium nitrite and potassium nitrite), nitrous halide, nitrous oxide, nitrous acid and nitrous anhydride. Sodium nitrite is preferred. An amount of HF corresponding to a ratio of at least 12 moles of HF per mole of sodium nitrite has been found sufficient. Sufficient amounts of HF for other diazotization agents can be readily determined by those skilled in the art.

The process of the present invention is based on the chemical reaction represented by the following illustrative equation:

$$Ar(NH_2)_m + 2\underline{m}HF + \underline{m}NaNO_2 =$$

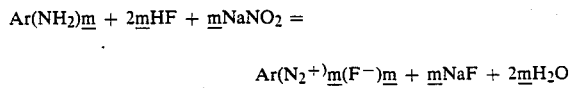

$$Ar(N_2^+)_{\underline{m}}(F^-)_{\underline{m}} + \underline{m}NaF + 2\underline{m}H_2O$$

where Ar is an aromatic moiety of the aromatic mono- or polyamine $Ar(NH_2)m$, m is an integer of 1, 2 or more and preferably is 1 or 2, and $NaNO_2$ illustrates the diazotization agent.

Hydrogen fluoride can act as both a reactant (e.g. a source of fluorine for the aromatic diazonium fluoride being prepared) and as the medium for the diazotization reaction. In order to serve as the reaction medium, there is employed an amount of HF in excess of the amount of HF required for use as such reactant. The amount of HF employed in each solution is preferably such that the total amount of HF in the amine-HF solution and nitrosyl fluoride solution introduced into the reactor results in introduction of from about (3+m) to about 30 moles and preferably from about 15+m to 20 moles of HF per mole of introduced amine where m is the number of diazotizable —NH$_2$ groups per molecule of the amine. In general, amounts of HF less than (3+m) moles per mole of amine result in unacceptably low autothermal decomposition temperatures, thereby risking uncontrollable reaction at otherwise desirable reaction temperatures and rates and/or requiring economically unacceptable reductions in reaction temperature and rate to safeguard against such risk. Amounts of more than 30 moles of HF per mole of amine generally result in unacceptably slow preparation of aromatic diazonium fluoride and/or unacceptably high cost of HF recovery. The hydrogen fluoride may be added as aqueous hydrofluoric acid containing, for example, from about 3 to about 30 or more percent by weight of water, preferably containing at least 70 percent by weight of HF (dry basis). However, better yields and greater freedom from tar, phenols and other by-products in subsequent decomposition of the diazonium fluoride to the aromatic fluoride can be obtained by employing at least substantially anhydrous hydrogen fluoride, i.e. not containing more than about 5% by weight water, and preferably not more than 0.1% water.

The aromatic amine is continuously introduced into a multi-stage reactor having a plurality of reaction zones, preferably at least 3. The amine, typically in the form of a solution, is preferably introduced at a temperature not substantially greater than 0° C. The nitrosyl fluoride is preferably introduced into each of the reaction zones at a temperature not substantially greater than 0° C.

In the most preferred embodiment of the invention, the reactor is a cross-flow tubular reactor having at least 3 reaction zones, each reaction zone having (i) an inlet for continuous injection of nitrosyl fluoride solution, (ii) a static mixer immediately downstream from said inlet and adapted for intimately mixing said solutions, and (iii) a tubular cooling zone downstream from said mixer for removing heat of diazotization.

While passing a flow of amine-HF solution through the tubular reactor, a flow of nitrosyl fluoride solution is continuously injected at a temperature of not substantially more than 0° C. through each inlet, whereby (i) the nitrosyl fluoride solution injected through the inlet of the most upstream reaction zone is intimately mixed in the static mixer thereof with the amine-HF solution introduced into the tubular reactor to form a first reaction mixture, (ii) the nitrosyl fluoride solution injected through each successive inlet is intimately mixed in each successive static mixer with the reaction mixture entering thereinto to form successive reaction mixtures in each successive reaction zone, (iii) in each reaction zone, an amount of amine which is approximately stoichiometrically equivalent to the amount of nitrosyl fluoride injected through the inlet thereof is diazotizingly reacted with the nitrosyl fluoride to (a) prepare a quantity of aromatic diazonium fluoride, and (b) generate a corresponding amount of heat, the ratio of total flow rate of nitrosyl fluoride solution to flow rate of amine solution corresponding to from about 0.9 to about 1.0 mole of nitrosyl fluoride per molar equivalent of amine, and the total amount of HF in the introduced amine-HF solution and injected nitrosyl fluoride solution being such that there are introduced from about $(3+m)$ to about 30 moles of HF per mole of amine where m is the number of diazotizable —$NH_2$ groups per molecule of said amine.

Heat is removed from each reaction zone in a sufficient amount and at a sufficient rate of heat transfer such that (a) the maximum temperature of the diazonium-fluoride-containing reaction mixture therein is less than the lower of (i) the autothermal decomposition temperature of said mixture, and (ii) the temperature at which said diazonium fluoride decomposes to such an extent and at such a rate that said aromatic diazonium fluoride is present in the reaction mixture exiting the cross-flow tubular reactor in an amount 5% less than the amount present when the maximum temperature in each reaction zone is 15° C., and (b) the temperature of the reaction mixture exiting each zone is not substantially more than 0° C.

Using the process of the invention, diazonium fluoride is prepared in an amount corresponding to at least 95% yield based on the nitrosyl fluoride employed. The resulting mixture exiting the tubular reactor is substantially free of nitrosyl fluoride and the diazonium fluoride can be decomposed in the resulting mixture with substantial freedom from formation of tar and other by-products.

The invention also provides a process for preparing an aromatic fluoride wherein the process further includes the step of decomposing the diazonium fluoride in said resulting mixture.

The invention can be further understood with reference to the drawing, which illustrates a preferred embodiment of the invention. The amine-HF solution and the nitrosyl fluoride solution may be prepared as described hereinabove in solution-preparation vessels 10 and 11, respectively. Each vessel preferably has heat exchange means (not shown) associated therewith for controlling the temperature of the solution contained therein. Such means may be, for example, a jacket disposed thereabout or a coil therein through which is passed a coolant, for example, a glycol/water solution.

A flow of amine-HF solution is continuously passed through conduit 12 via pump 14, flow meter 16, flow control valve V(17) and check valve 21 and continuously introduced into cross-flow tubular reactor 20. The introduced flow is maintained at a temperature of not substantially more than 0° C., e.g. not more than 10° C. and preferably not more than 5° C. A temperature of 0° C. is most preferred. Heat exchanger 18 may be employed to control such temperature.

The cross-flow tubular reactor has a plurality of n sequential reaction zones 22 wherein n is an integer of at least 3, preferably at least 4 and more preferably at least 5. Each reaction zone or section has an inlet 24 provided with flow meter 26 and check valve 28 for injection of the nitrosyl fluoride solution; a static mixer 30 disposed immediately downstream from said inlet and adapted for intimately mixing the amine-HF solution and the nitrosyl fluoride solution; and a tubular cooling zone or section 31 downstream from the mixer for removing heat of diazotization. The introduced flow of amine-HF solution passes generally axially through the cross-flow reactor.

Suitable static mixers which can be utilized in the practice of the present invention are Chemineer-Kenics Static Mixer, which are available from Kenics Corporation, North Andover, Mass. The internal surfaces of the static mixers employed herein are preferably teflon coated, i.e. the inner surface of the tubular housing and the surfaces of the mixing elements preferably are of teflon. Type 316 stainless steel is also suitable, but teflon provides increased resistance to corrosion. The inside diameter of the tubular housing and of the tubular cooling section downstream of the mixer may be, for example, from about 0.25 inch or less to about 12 inches or more.

While passing the flow of amine-HF solution through the tubular reactor, a flow of the nitrosyl fluoride solution is injected or introduced into the amine-HF flow through each inlet. The nitrosyl fluoride solution (NOFS) is continuously passed through conduit 13 via pump 15 to supply the individual flows to the inlets. The NOFS is introduced at a temperature of not substantially more than 0° C., e.g. not more than 10° C. and preferably not more than 5° C. A temperature of 0° C. is most preferred. Heat exchange 19 may be employed to control the NOFS inlet temperature.

Although the reaction zones may be of unequal lengths, preferably the reaction zones are of equal length such that the inlets for the nitrosyl fluoride solution are spaced uniformly apart axially of the reactor.

The ratio of the flow rate of the NOFS to the flow rate of the amine-HF solution is maintained at an amount corresponding to slightly less than 1.0 mole of nitrosyl fluoride per molar equivalent of the amine and preferably at about 0.98 mole of nitrosyl fluoride per molar equivalent of the amine. The total amount of HF in the introduced amine-HF solution and in the injected NOFS is controlled such that there are introduced from about $3+m$ to about 30 moles of HF per mole of amine where m is the number of diazotizable —$NH_2$ groups per molecule of the amine.

Although the individual flow rates of nitrosyl fluoride solution introduced through each inlet may be unequal, preferably such rates are equal each to the other. As a general preference, the n reaction zones are of approximately equal length and approximately 1/n of the total flow of nitrosyl fluoride solution is introduced through each inlet into a reaction zone, n being defined above. Preferably, the tubular reactor includes 10 reaction zones of approximately equal length and about 1/10th (one-tenth) of the total flow of nitrosyl fluoride solution is introduced through each of the 10 inlets, which are spaced approximately equidistantly one from another. As a result of static mixing action, the nitrosyl fluoride solution injected through the inlet of the most upstream reaction zone is intimately mixed in the static mixer thereof with the amine-HF solution introduced into the tubular reactor to form a first reaction mixture. Similarly, the nitrosyl fluoride solution injected through each successive inlet is intimately mixed in each successive static mixer with the reaction mixture entering thereinto to form successive reaction mixtures in each successive reaction zone. In each reaction zone, an amount of the amine which is approximately stoichiometrically equivalent to the amount of nitrosyl fluoride injected through the inlet thereof diazotizingly reacts with the nitrosyl fluoride to (a) prepare a quantity of the corresponding aromatic diazonium fluoride, and (b) generate a corresponding amount of heat of diazotization.

In general, from about 98% to about 100% of the introduced nitrosyl fluoride is converted to the corresponding diazonium fluoride.

Heat is removed from one or more of the reaction zones, preferably from each reaction zone, in a sufficient amount and at a sufficient rate such that (a) the maximum temperature of the diazonium-fluoride-containing reaction mixture therein is less than the lower of (i) the autothermal decomposition temperature of the mixture, and (ii) the temperature at which the diazonium fluoride decomposes to such an extent and at such a rate that the diazonium fluoride is present in the reaction mixture exiting the cross-flow tubular reactor in an amount 5% less than the amount present when the maximum temperature in each reaction zone is 15° C., and (b) the temperature of the reaction mixture exiting each zone is not substantially more than 0° C.

Figure 3:
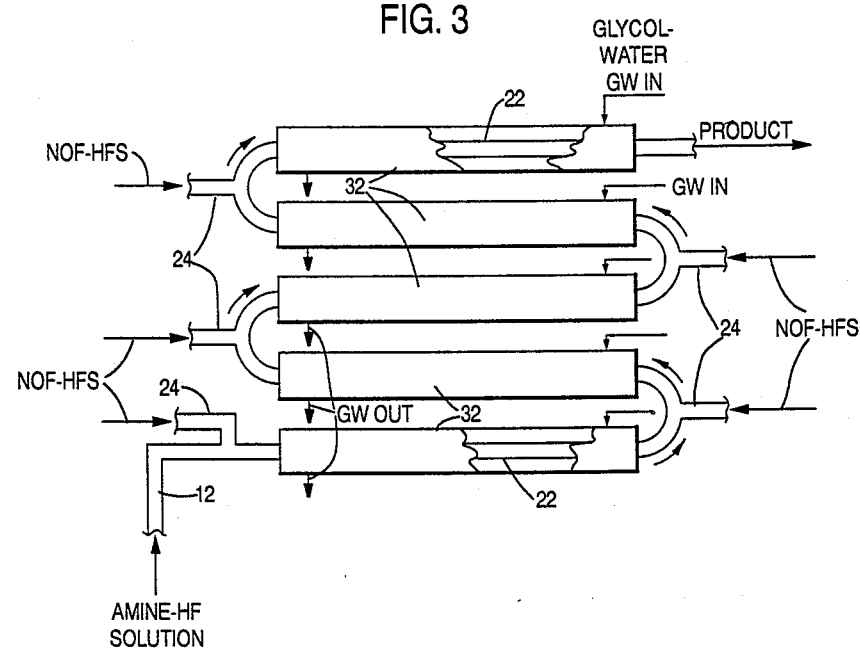
FIG. 3 illustrates an embodiment of the invention wherein each reaction section is provided with a separate cooling jacket.

Removal of heat can be by means of a cooling bath (not shown) into which the tubular reactor is immersed. Preferably, heat removal is effected by means of flowing a coolant (e.g. 50% glycol and 50% water supplied at minus 5° C. or less) through separate cooling jackets 32, each jacket disposed about a separate section of the reactor 20 (i.e. about a separate reaction zone) as shown in FIG. 3.

Means of temperature control other than heat removal from the reaction zones can also be employed to control the temperature of the reaction mixture. For example, a portion of the product emerging from the last reaction zone, or from an intermediate reaction zone, may be recycled to the inlet of one or more of the upstream reaction zones, after passing it through a heat exchanger to reduce its temperature. The recycled mixture will absorb heat from the reaction mixture in the reaction zone, thereby assisting in the control of temperature in the reaction zone and reducing the number of injection stages.

Figure 4:
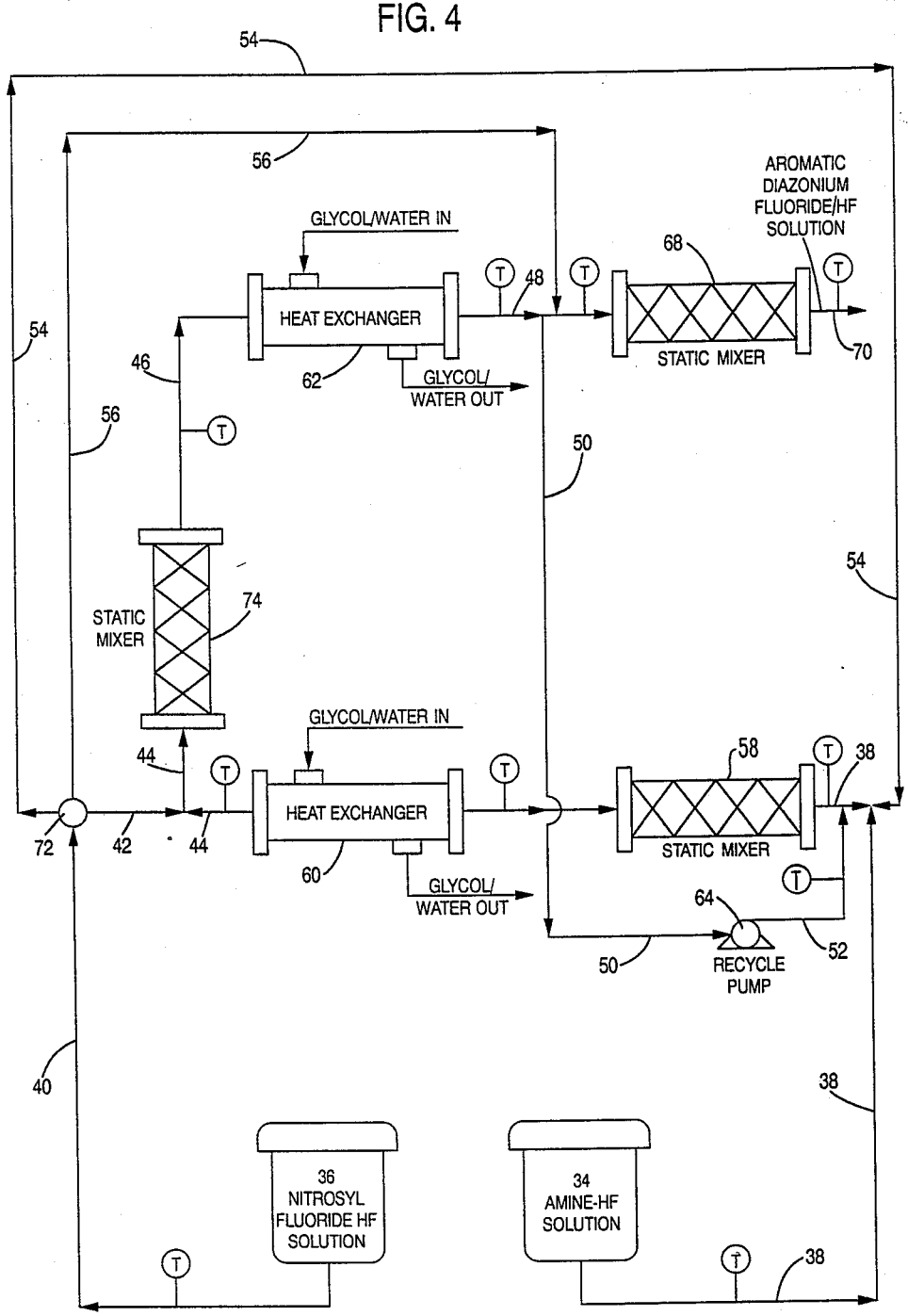
FIG. 4 is a schematic illustration of an embodiment of the process of the invention which employs recycle of reactor product to assist in temperature control.

FIG. 4 schematically illustrates an embodiment of the invention which employs recycle of reactor product to assist in temperature control. For the sake of simplicity, in the schematic diagram various valves, gauges, meters, control devices and other ancillary equipment have not been shown. Aniline-HF solution is prepared in tank 34 in a manner similar to that previously described. The aniline-HF solution is fed continuously under pressure through line 38 and thence into static mixer 58. NOFS, which is prepared in a manner similar to that previously described, is continuously fed under pressure from tank 36 through line 40 to a rotameter 72 which divides the flow of NOFS into three streams. One stream is continuously fed via line 54 into line 38 immediately prior to static mixer 58. A second stream of NOFS is fed via line 42 into line 44 just prior to its entry into static mixer 74. A third stream of NOFS is fed via line 56 into line 48 immediately prior to its entrance into static mixer 68. The flow rate of aniline-HF solution is controlled by a set point on a controller (not shown) the flow rate of NOFS from tank 36 is controlled by a ratio controller (not shown) driven by the aniline-HF flow. By appropriate adjustment of the ratio controller and the rotameter 72, it is possible to control the overall ratio of NOFS to aniline-HF solution entering the multi-stage reactor as well as to control the proportions of the NOFS flow that are fed to each individual static mixer.

The amine-HF solution and NOFS entering static mixer 58 are admixed and reacted therein to produce a mixture containing diazonium flouride which is then passed to a heat exchanger 60 to remove heat of diazotization. The cooled product is fed via line 44 to static mixer 74 where it is admixed and reacted with NOFS entering from line 42. The reaction product, containing an increased proportion of diazonium flouride, passes via line 46 through heat exchanger 62 into line 48. A portion of the cooled reaction product is withdrawn via line 50 through recycle pump 64 and thence into line 52 by which it is recycle into line 38 immediately prior to its entry into static mixer 58. The remainder of the reaction product in line 48 is fed to static mixer 68 where it is admixed and reacted with NOFS entering the static mixer via line 56. The reaction product exits static mixer 68 at line 70. By using the rotameter 72 to adjust the relative proportions of NOFS flowing to the three static mixers, it is possible to eliminate the need for a heat exchanger to adjust the temperature of the reaction product exiting static mixer 68.

It is critical that the maximum temperature of the reaction mixture containing diazonium fluoride be maintained at less than the autothermal decomposition temperature of the mixture. For a given system, such temperature decreases with increasing concentration of the diazonium fluoride being prepared. In general, the concentration of diazonium fluoride may safely be up to about 3 gram-moles per liter (g-moles/l), e.g. from about 0.1 to 3 g-moles/l, preferably from about 1.5 to 2.5 g-moles/l and more preferably from about 2.0 to 2.5 g-moles/l.

Where aniline is the amine being diazotized and the resulting benzene diazonium fluoride is present in a concentration of up to about 2.5 g-moles/l in the reaction mixture exiting the reactor, the maximum temperature of the reaction mixture in the reaction zones corresponding to approximately 40% of the upstream length of the reactor may be up to about 25° C., while the maximum temperature of the reaction mixture in the downstream remainder of the reactor may be up to about 15° C. The indicated temperatures may be held at or below such maximums by balancing the heat load (which depends on rate of reaction and flow rate) and heat removal capacity of the temperature control system.

According to Behringer, et al. (U.S. Pat. No. 4,268,437 supra), if an amine rapidly undergoes diazotization, it is good practice to introduce the aqueous sodium nitrite solution exclusively through one inlet in the continuous diazotization process disclosed therein. In contrast, in the process of the present invention, a solution of nitrosyl fluoride in HF is advantageously introduced through a plurality of inlets for all amines, including amines which rapidly undergo diazotization (e.g. 3,3'-dichlorobenzidine, aniline, 2-chloro-o-toluidine, 4-fluoroaniline and methylene dianiline).

The heat capacity of HF is approximately half the heat capacity of water. Therefore, a given heat load (e.g. amount of generated heat of diazotization) has the potential to increase the temperature of a given mass of HF by an amount which is approximately double the potential temperature increase for a like mass of water. This phenomenon is sometimes referred to herein as the double delta-T effect.

It will be appreciated by those skilled in the art that this double delta-T effect results in a considerably greater temperature-control burden on the present process relative to diazotization processes carried out in predominantly aqueous media (a number of which are referenced above), especially where, as preferred, at least substantially anhydrous hydrogen fluoride is employed in the present process. Advantageously, the process of the present invention effectively bears such burden without detracting from the effective utility thereof. In general, the flow rate of the amine-HF solution is such that the average residence time thereof in the reactor is from about 0.5 minute to about 10 minutes.

Practice of this invention is further illustrated by the following non-limiting examples. All parts, percents and other amounts throughout this disclosure are by weight unless otherwise indicated.

EXAMPLE 1

Diazotization of Aniline in a Cross-Flow Tubular Reactor

Aniline, 9.11 kilograms (kg), i.e. 98.0 gram-moles (g-moles), was added with stirring to 11.77 kg (588.5 g-moles) of hydrogen fluoride (HF) in vessel 10, while maintaining the resulting mixture at a temperature of 5° C. via cooling water, thereby forming a solution of aniline in HF having a 6:1 molar ratio of HF to aniline. Next, sodium nitrite, 6.62 kg (96.0 g-moles), was added with stirring to 23.04 kg (1152 g-moles) of HF in vessel 11, while maintaining the resulting mixture at a temperature of 2° C. via cooling water, thereby forming a solution of nitrosyl fluoride in HF having a 12:1 molar ratio of HF to nitrosyl fluoride.

Then, a total of 18 liters (20.9 kg) of the aniline-HF solution was introduced continuously for one hour, via pump 14, at a flow rate of 300 milliliters per minute) and at an inlet temperature of 0°-2° C. into a (1.63 g-moles of aniline and 9.81 g-mole of HF per cross-flow tubular reactor 20 having a total length of 110 feet. The reactor consisted of 10 sequentially adjacent, identical reaction-zone sections, each having an inside diameter of 0.305 inch. Each such section contained a Kenics 316 stainless steel tubular static mixer, 12 inches in length and ⅜ inch I.D. (Kenics Corporation, Kenics Park, North Andover, Mass.), the mixer having a lateral inlet immediately upstream of, and adjacent to, its first mixing element, and a 316 stainless steel tube (0.305 inch in I.D. and 10 feet in length) immediately downstream of the mixer to serve as a cooling section. A pressure control valve was disposed at the downstream end of the last section to maintain the tubular reactor full of liquid. During such hour, a total of 19,920 ml of the HF solution of nitrosyl fluoride was continuously injected into the reactor at 2° C. and a total flow rate of 332 milliliters per minute (1.60 g-moles of nitrosyl fluoride per minute and 16.0 g-moles of HF per minute) via 10 approximately equal flows of 30 to 35 ml/minute, each such flow being introduced through a corresponding inlet of a different static mixer. There were thus introduced, per g-mole of aniline, 0.98 g-mole of nitrosyl fluoride and 17.45 g-moles of HF. The temperature of the resulting exothermic diazotizing reaction mixture was controlled by a refrigerated bath of glycol and water maintained at −5° C. into which the cross-flow tubular reactor 20 was immersed. The bath temperature was maintained such that (a) the temperature of the reaction mixture entering the second and each successive static mixer was about 5° C.; (b) the temperature of the reaction mixture exiting each static mixer in the first four sections was about 25° C. (maximum temperature in each such section); and (c) the temperature of the reaction mixture exiting each static mixer in the last six sections was about 15° C. (the maximum temperature in each such section). The average residence time of the amine-HF solution in the reactor was about 4 minutes.

The resulting mixture exiting the tubular reactor was a clear brownish-orange solution, which was collected for further processing. Analysis of samples taken at 5-minute intervals of the stream exiting the reactor showed the presence therein of benzene diazonium fluoride in concentrations ranging from about 2.36 to 2.41 g-moles thereof per liter, corresponding to a diazonium fluoride yield of 98 to 100% based on the amount of nitrosyl fluoride introduced into the reactor. Inasmuch as the nitrosyl fluoride was introduced in an amount corresponding to 0.98 g-mole per 1.00 g-mole of introduced aniline, this corresponds to from 2 to 4% of the introduced aniline remaining unconverted in the product stream.

The collected product mixture containing benzene diazonium fluoride can be used to decompose the diazonium fluoride (i.e. liberate nitrogen gas and form fluorobenzene) using known methods for decomposing diazonium fluorides, e.g. heating the mixture with refluxing at about 40° C. to 50° C. until nitrogen evolution ceases.

EXAMPLE 2

The procedure of Example 1 was repeated except that the total flow of HF solution of nitrosyl fluoride was injected via 7 approximately equal flows of 43 to 50 ml/minute through the inlets of the 7 downstream static mixers and the temperature of the refrigerated bath of glycol and water was maintained at minus 8° C.

The temperature of the reaction mixture entering the second and each successive static mixer was essentially unchanged (about 5° C.); the temperature of the reaction mixture exiting each static mixer in the first four sections was unchanged (about 25° C.); and the temperature of the reaction mixture exiting each static mixer in the three downstream sections into which the fifth, sixth and seventh flows of the nitrosyl fluoride solution were injected was about 15° C. (the maximum temperature in each such section).

The resulting mixture exiting the tubular reactor was substantially the same as the resulting mixture in Example 1, including (a) clear brownish-orange solution, (b) concentrations of benzene diazonium fluoride of about 2.36 to 2.41 g-moles per liter, and (c) diazonium fluoride yield of 98 to 100% based on the amount of nitrosyl fluoride introduced into the reactor.

EXAMPLE 3

Benzene diazonium fluoride was prepared substantially in accordance with the procedure of Example 1 except that the temperature of the refrigerated bath of glycol and water was maintained at plus 5° C.

The temperature of the reaction mixture exiting each static mixer in the first four sections was higher (35° C., maximum temperature in each such section). The temperature of the reaction mixture exiting each static mixer in the last six sections was also higher (about 20° C., maximum temperature in each such section).

The resulting mixture exiting the cross-flow tubular reactor was a dark brownish-black solution. Analysis of the samples of the exiting stream showed presence of benzene diazonium fluoride in lower concentrations of from about 2.05 to about 2.17 g-moles per liter, corresponding to a diazonium fluoride yield of about 85 to 90% based on the amount of nitrosyl fluoride introduced into the reactor.

EXAMPLE 4

Diazotization of Aniline in a Cross-Flow Recycle Reactor 9.11 kg (97.96 g-moles) of aniline was added with stirring to 11.77 kg (588.5 g-moles) of HF in tank 34 while maintaining a temperature of 5° C. via cooling water, thereby forming a solution of aniline-HF at a 1 to 6 molar ratio. Then 6.76 kg (97.97 g-moles) of sodium nitrite were added with stirring to 23.51 kg (1173 g-moles) of HF in tank 36 while maintaining a temperature of 2° C. via cooling water, thereby forming a solution of nitrosyl fluoride in HF at a 1 to 12 molar ratio.

The aniline-HF solution was fed continuously to the multi-stage reactor for one hour at 25° C. at a flow rate of 200 ml/min. Once the multi-stage reactor was filled with aniline-HF the recycle pump 64 was set to deliver 2,050 ml/min. or a 4.81 mass ratio of recycled to total mass in. The nitrosyl fluoride-HF solution was injected incrementally into lines 38, 44 and 48 immediately prior to each of the three static mixers. The proportions of nitrosyl fluoride fed to static mixer 58, 74 and 68 respectively, were 50%, 40% and 10%.

The nitrosyl fluoride solution was fed continuously for one hour at 10° C. by pressurizing tank 36 and controlling the flow rate at 209 ml/min. via a control valve (not shown) allowing approximately 7% of the feed aniline to exit at 70 unconverted.

The temperature of the reaction mixture was maintained by pumping a solution of glycol and water, maintained at 5° C. by a chiller, through heat exchangers 60 and 62. The cooling solution flow was maintained such that the temperature of the reaction mixture was between 5 and 25° C. in the first two reaction sections and between 5 and 18° C. in the third reaction section. The completely reacted reaction mixture leaving the recycle reactor was a clear brownish-orange solution that was collected for further processing to produce fluorobezene. Test samples of the reaction mixture were collected every five minutes. Of the samples taken, the concentration of benzene diazonium fluoride was between 2.59 g-mole/liter and 2.61 g-mole/liter, corresponding to a conversion of between 98% and 100% of aniline to benzene diazonium fluoride, based on nitrosyl fluoride injected.

Best Mode Contemplated

The best mode contemplated for carrying out this invention has been set forth in the above description, for example, by way of setting forth preferred materials and operating conditions, including, but not limited to, preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

I claim:

1. A process for the continuous production of an aromatic diazonium fluoride compound from the corresponding aromatic amine which comprises continuously introducing an aromatic amine into a multi-stage reactor comprising a plurality of sequential reaction zones; continuously introducing nitrosyl fluoride into each reaction zone and admixing it with aromatic amine therein, thereby reacting a portion of the aromatic amine with nitrosyl fluoride to form aromatic diazonium fluoride; and controlling the temperature in each reaction zone by means of a heat exchanger in each reaction zone such that the maximum temperature of the reaction mixture in each reaction zone is less than the autothermal decomposition temperature of the mixture and that the aromatic diazonium fluoride undergoes substantially no thermal decomposition.

2. A process as claimed in claim 1, wherein the ratio of the flow rate of aromatic amine to the sum of the flow rate of nitrosyl fluoride into the reaction zones is such that at least 95% of the nitrosyl fluoride is reacted to form diazonium fluoride.

3. The process of claim 1, wherein the multi-stage reactor is a cross-flow tubular reactor.

4. The process of claim 1, wherein the aromatic amine is in the form of a solution in hydrogen fluoride.

5. The process of claim 1, wherein the nitrosyl fluoride is formed by dissolving a diazotization agent selected from the group consisting of alkali metal nitrite, nitrous acid, nitrous anhydride, nitrous halide, and nitrous oxide in liquid hydrogen fluoride.

6. The process of claim 1, wherein said aromatic amine is selected from the group consisting of carbocyclic aromatic primary amines and heterocyclic aromatic primary amines.

7. The process of claim 5, wherein said carbocyclic amines are derivatives of carbocyclic compounds selected from the group consisting of benzene, biphenyl, diphenylmethane, diphenyl ether, naphthalene and anthracene, and said heterocyclic amines are derivatives of heterocyclic compounds selected from the group consisting of pyridine, quinoline and isoquinoline.

8. The process of claim 6, wherein said carbocyclic amines are selected from the group consisting of aniline, methoxyaniline, chloroaniline, bromoaniline, toluidine, ring-halogenated toluidine, phenylene diamine, methylene dianiline and biphenyl amine, and said heterocyclic amines are selected from the group consisting of aminopyridine diaminopyridine, haloaminopyridine, nitroaminopyridine and $C_1$ to $C_8$ alkylaminopyridine.

9. The process of claim 6, wherein said aromatic amine is selected from the group consisting of aniline, 2-chloro-toluidine, 4-fluoroaniline and methylene dianiline.

10. The process of claim 9, wherein said amine is aniline and said diazonium fluoride is benzene diazonium fluoride.

11. The process of claim 1, which further comprises after the resulting mixture exits the reactor, decomposing the aromatic diazonium fluoride in said resulting mixture, thereby forming the corresponding aromatic fluoride in said mixture with substantial freedom from formation of tar and other by-products.

12. A process for the continuous preparation of an aromatic diazonium fluoride compound from the corresponding aromatic amine, which comprises:
    (a) continuously introducing a flow of a solution of said amine in hydrogen fluoride into a cross-flow tubular reactor comprising a plurality of sequential reaction zones;
    (b) continuously introducing into the upstream portion of each reaction zone a flow of a nitrosyl fluoride;
    (c) mixing the amine solution and the nitrosyl fluoride in each reaction zone, thereby reacting the amine and the nitrosyl fluoride to form aromatic diazonium fluoride; and
    (d) removing heat from one or more of the reaction zones by means of heat exchanger in each reaction zone at a sufficient rate that the maximum temperature of the reaction mixture in each reaction zone is less than the autothermal decomposition temperature of said mixture and that the diazonium fluoride undergoes substantially no thermal decomposition, provided that the ratio of the flow rate of aromatic amine into the cross-flow tubular reactor to the sum of the flow rates of nitrosyl fluoride into the sequential reaction zones is such that at least 95 mole % of the nitrosyl fluoride is reacted to form diazonium fluoride.

13. The process of claim 12, wherein the cross-flow tubular reactor comprises n sequential reaction zones, wherein n is an integer having a value of at least 3.

14. The process of claim 12, wherein the n reaction zones are of approximately equal length.

15. The process of claim 14, wherein approximately 1/n of the total flow of nitrosyl fluoride solution is introduced through each inlet.

16. The process of claim 14, wherein n is at least

17. The process of claim 16, wherein n is at least 5.

18. The process of claim 12, wherein said amine is aniline, said diazonium fluoride is benzene diazonium fluoride present at a concentration of up to about 2.5 gram-moles per liter in the reaction mixture exiting the reactor, the maximum temperature of the reaction mixture in the reaction zones corresponding to up to approximately 40% of the upstream length of the reactor is up to about 25° C., and the maximum temperature of the reaction mixture in the downstream remainder of the reactor is up to about 15° C.

19. The process of claim 18, wherein the aniline-HF solution comprises at least 6 moles of HF per mole of aniline, the solution of nitrosyl fluoride is prepared from sodium nitrite and HF in an amount corresponding to at least 12 moles of HF per mole of sodium nitrite, n is at least 5 and the average residence time of the amine-HF solution in the reactor is from about 0.5 to 10 minutes.

20. The process of claim 19, wherein n is at least 7.

21. The process of claim 19, wherein n is at least 10.

22. The process of claim 12, wherein a portion of the product exiting one or more of the reaction zones and passed through a heat exchanger to reduce its temperature is then recycled to an upstream reaction zone.

* * * * *

UNITED STATES PATENT AND TRADEMARK OFFICE
CERTIFICATE OF CORRECTION

PATENT NO. : 4,918,168
DATED : April 17, 1990
INVENTOR(S) : Nicholas J. STEPANIUK et al.

It is certified that error appears in the above-identified patent and that said Letters Patent is hereby corrected as shown below:

```
Col.  4, line 44, "polyamnnes" should be --polyamines--.
Col. 11, line 47, after "minute" and before")" insert
        --(1.63 g-moles of aniline and 9.81 g-mole of
   HF per minute--;
        line 48, delete "(1.63 g-moles";
        line 49, delete (of aniline and 9.81 g-mole of
        HF per".
Col. 15, line 21, after "of" insert --a--.
Col. 16, line  9, after "lease" insert --4.--.
```

Signed and Sealed this

Second Day of July, 1991

Attest:

HARRY F. MANBECK, JR.

*Attesting Officer*     Commissioner of Patents and Trademarks